United States Patent
Wu et al.

(10) Patent No.: US 7,609,377 B2
(45) Date of Patent: Oct. 27, 2009

(54) SURFACE ENHANCED RAMAN SPECTROSCOPY WITH PERIODICALLY DEFORMED SERS-ACTIVE STRUCTURE

(75) Inventors: Wei Wu, Mountain View, CA (US); Zhiyong Li, Palo Alto, CA (US); Shih-Yuan Wang, Palo Alto, CA (US); Zhaoning Yu, Mountain View, CA (US); R. Stanley Williams, Portola Valley, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 403 days.

(21) Appl. No.: 11/796,455

(22) Filed: Apr. 26, 2007

(65) Prior Publication Data

US 2008/0270042 A1    Oct. 30, 2008

(51) Int. Cl.
*G01J 3/44*    (2006.01)
(52) U.S. Cl. .................................... 356/301
(58) Field of Classification Search ............. 356/301
See application file for complete search history.

(56) References Cited

U.S. PATENT DOCUMENTS

| 7,016,034 | B2 | 3/2006 | Holz et al. |
| 7,145,651 | B2 | 12/2006 | Li et al. |
| 2006/0197953 | A1 | 9/2006 | Perez et al. |
| 2006/0250613 | A1 | 11/2006 | Demuth et al. |
| 2007/0086001 | A1* | 4/2007 | Islam et al. ............... 356/301 |
| 2008/0024776 | A1* | 1/2008 | Bratkovski et al. ......... 356/301 |

OTHER PUBLICATIONS

Lu, Y., et. al., "High-Density Silver Nanoparticle Film with Temperature-Controllable Interparticle Spacing . . . ", Nano Letters, vol. 5, No. 1, pp. 5-9 (Dec. 2004).

Hung, P., et. al., "Microfabricated Suspensions for Electrical Connections on the Tunable Elastomer Membrane," App. Phys. Lett., vol. 85, No. 24, pp. 6051-6053 (Dec. 2004).

* cited by examiner

*Primary Examiner*—Kara E Geisel (57) ABSTRACT

An apparatus and related methods for facilitating surface-enhanced Raman spectroscopy (SERS) is described. A SERS-active structure near which a plurality of analyte molecules is disposed is periodically deformed at an actuation frequency. A synchronous measuring device synchronized with the actuation frequency receives Raman radiation scattered from the analyte molecules and generates therefrom at least one Raman signal measurement.

20 Claims, 6 Drawing Sheets

SURFACE ENHANCED RAMAN SPECTROSCOPY WITH PERIODICALLY DEFORMED SERS-ACTIVE STRUCTURE

FIELD

This patent specification relates to Raman spectroscopy. More particularly, this patent specification relates to Surface Enhanced Raman Spectroscopy (SERS) in which SERS-active structures are used to intensify Raman signals from analyte molecules disposed adjacent thereto or adsorbed thereonto.

BACKGROUND

Raman spectroscopy is a technique for performing chemical analysis. High intensity monochromatic light, such as that provided by a laser, is directed onto an analyte molecule (or sample) that is to be chemically analyzed. A majority of the incident photons are elastically scattered by the analyte molecule, wherein the scattered photons have the same energy (and, therefore, the same frequency) as the incident photons. This elastic scattering is termed Rayleigh scattering, and the elastically scattered photons and radiation are termed Rayleigh photons and Rayleigh radiation, respectively. However, a small fraction of the photons (e.g., about 1 in $10^7$ photons) are inelastically scattered by the analyte molecules. These inelastically scattered photons have a different frequency than the incident photons. This inelastic scattering of photons is termed the Raman effect. The inelastically scattered photons may have frequencies greater than, or, more typically, less than the frequency of the incident photons.

When an incident photon collides with a molecule, energy may be transferred from the photon to the molecule or from the molecule to the photon. When energy is transferred from the photon to the molecule, the scattered photon will emerge from the sample having a lower energy and a corresponding lower frequency. These lower-energy Raman scattered photons are commonly referred to in Raman spectroscopy as the Stokes radiation. A small fraction of the analyte molecules are already in an energetically excited state. When an incident photon collides with an excited molecule, energy may be transferred from the molecule to the photon, which will emerge from the sample having a higher energy and a corresponding higher frequency. These higher-energy Raman scattered photons are commonly referred to in Raman spectroscopy as the anti-Stokes radiation.

The Stokes and the anti-Stokes radiation is detected by a detector, such as a photomultiplier or a wavelength-dispersive spectrometer, which converts the energy of the impinging photons into an electrical signal. The characteristics of the electrical signal are at least partially a function of the energy (or wavelength, frequency, wave number, etc.) of the impinging photons and the number of the impinging photons per unit time (intensity). The electrical signal generated by the detector can be used to produce a spectral graph of intensity as a function of frequency for the detected Raman signal (i.e., the Stokes and anti-Stokes radiation). A unique Raman spectrum corresponding to the particular analyte may be obtained by plotting the intensity of the inelastically scattered Raman photons against their frequency or, equivalently and more commonly, their wavenumber in units of inverse centimeters. This unique Raman spectrum may be used for many purposes such as identifying an analyte, identifying chemical states or bonding of atoms and molecules in the analyte, and determining physical and chemical properties of the analyte. Raman spectroscopy may be used to analyze a single molecular species or mixtures of different molecular species. Furthermore, Raman spectroscopy may be performed on a number of different types of molecular configurations, such as organic and inorganic molecules in either crystalline or amorphous states.

Molecular Raman scattering of photons is a weak process. As a result, powerful, costly laser sources typically are used to generate high intensity excitation radiation to increase the weak Raman signal for detection. Surface enhanced Raman spectroscopy (SERS) is a technique that allows for generation of a stronger Raman signal from an analyte relative to non-SERS Raman spectroscopy for a sample with the same number of analyte molecules. In SERS, the analyte molecules are adsorbed onto, or placed adjacent to, an activated metal surface or structure, termed herein a SERS-active structure. The interactions between the molecules and the surface cause an increase in the strength of the Raman signal. Several SERS-active structures have been employed in SERS techniques, including activated electrodes in electrolytic cells, activated metal colloid solutions, and activated metal substrates such as a roughened metal surface or metal islands formed on a substrate. For example, it has been shown that adsorbing analyte molecules onto or near a specially roughened metal surface made from silver or gold may enhance the Raman scattering intensity by factors of between $10^3$ and $10^6$. As used herein, SERS-active material refers to the metallic material (or other material that can be found to have a similar effect) that is distributed across the substrate to form the SERS-active structures.

Although theories such as electromagnetic enhancement and chemical enhancement are set forth in the literature, the mechanism of Raman signal enhancement exhibited in SERS is not completely understood. Empirically, it has been observed that the intensification of the Raman scattered photons from analyte molecules can be sensitive to small variations in the localized configurations (e.g., spacings, relative orientations, etc.) of the localized structures, islands, bumps, or cavities of the SERS-active material. Issues arise in relation to the development of practical SERS-based measurement devices. Other issues arise as would be apparent to one skilled in the art upon reading the present disclosure.

SUMMARY

In one embodiment, an apparatus for facilitating surface-enhanced Raman spectroscopy (SERS) is provided, comprising a SERS-active structure near which a plurality of analyte molecules is disposed, and further comprising an actuation device in actuable communication with the SERS-active structure. The actuation device periodically deforms the SERS-active structure at an actuation frequency. A synchronous measuring device receives Raman radiation scattered from the analyte molecules and generates therefrom at least one Raman signal measurement. The synchronous measuring device is synchronized with the actuation frequency.

Also provided is a method for facilitating surface-enhanced Raman spectroscopy (SERS), comprising receiving a plurality of analyte molecules for attachment near a SERS-active structure and periodically deforming the SERS-active structure at an actuation frequency in a vicinity of the analyte molecules. Raman radiation scattered from the analyte molecules is received at a synchronous measuring device that generates at least one Raman signal measurement therefrom. The synchronous measuring device is synchronized with the actuation frequency.

Also provided is an apparatus, comprising a SERS-active structure near which a plurality of analyte molecules is disposed, and means for detecting Raman radiation scattered from the analyte molecules. The apparatus further comprises means for periodically deforming the SERS-active structure at an actuation frequency to cause an output of the means for detecting to be periodic at the actuation frequency. The apparatus further comprises means for synchronous processing of the output of the means for detecting to generate therefrom a Raman signal measurement. The means for synchronous processing uses a reference frequency equal to the actuation frequency.

DETAILED DESCRIPTION

Figure 1:
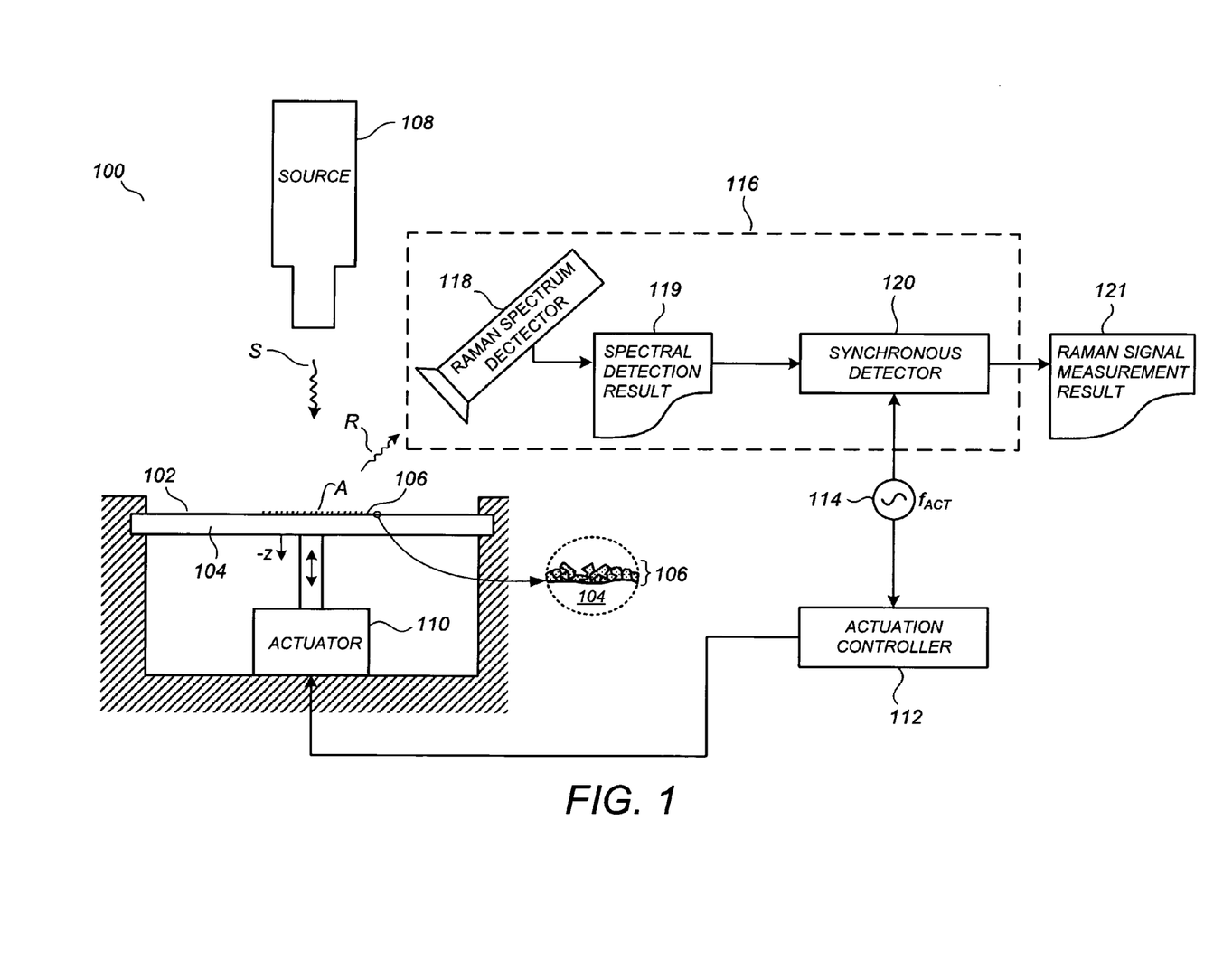
FIG. 1 illustrates a surface-enhanced Raman spectroscopy (SERS) system including an apparatus for facilitating SERS according to an embodiment.
Figure 2A:
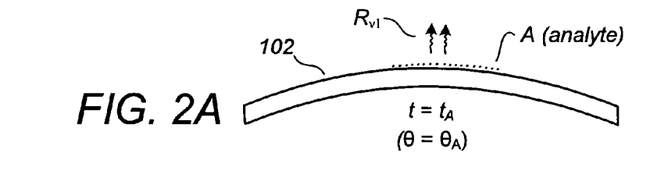
FIGS. 2A-2E illustrate a SERS-active structure at different amounts of deformation according to an embodiment.
Figures 2B, 2C:
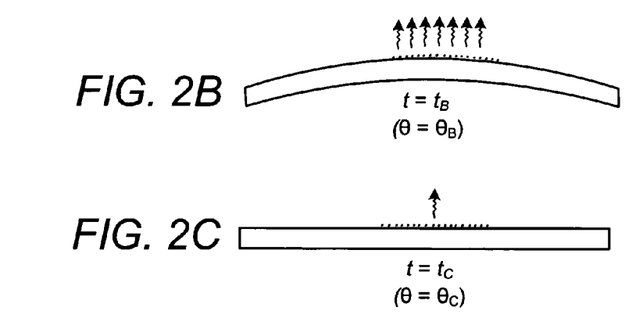
Figure 2D:
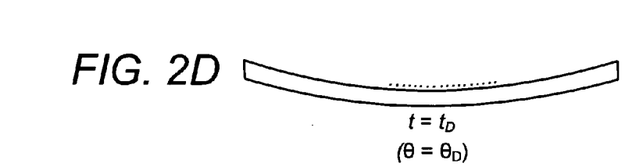
Figure 2E:
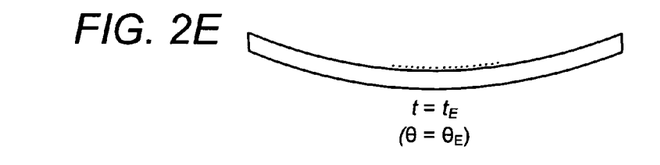

FIG. 1 illustrates a surface-enhanced Raman spectroscopy (SERS) system 100 including an apparatus for facilitating SERS according to an embodiment. SERS system 100 comprises a SERS-active structure 102 upon which analyte molecules "A" are disposed, as well as a radiation source 108 that irradiates the analyte molecules "A" with a strong monochromatic light beam "S." For clarity of description, the scattered radiation "R" illustrated in FIG. 1 is referenced herein as Raman radiation, it being understood that both elastically (Rayleigh) and inelastically (Raman) scattered radiation are usually present. The elastically scattered radiation is generally not of interest for SERS purposes and is usually filtered as part of the Raman radiation detection process.

The light beam "S" typically has a spot size of about 1 μm-5 μm. An exemplary range of wavelengths that may be emitted by the radiation source 108 includes wavelengths between about 350 nm and about 1000 nm. Raman radiation is often expressed in terms of one or more features of a plot of intensity versus Raman shift, the Raman shift being defined as a difference vbetween the wavenumbers of the source radiation S and Raman-scattered radiation R. Peaks and valleys of such plots that are meaningful for purposes of chemical analysis are often for Raman shifts in the range of 500 cm$^{-1}$-2000 cm$^{-1}$, which for a typical source wavelength of 1000 nm would correspond to Raman-scattered photons having wavelengths between 1050 nm-1250 nm.

SERS-active structure 102 comprises a substrate 104 having a arrangement of SERS-active material 106 thereon. The SERS-active material 106 can comprise chemically prepared metallic colloids, a roughened metallic surface, a structured or random array of metal-coated nanowires, or any of a variety of other material preparations known to be SERS-active. Examples of suitable SERS-active materials include gold, silver, copper, platinum, palladium, titanium, and aluminum. The SERS-active structure 102 is preferably derivatized or functionalized by attachment of receptors or ligands (not shown) that promote the binding of a particular analyte molecule in close proximity to the SERS-active material 106. The ligand may be repulsive or neutral relative to other molecules. The ligand and the analyte molecule may consist of what is often referred to as a specific pair or a recognition pair of molecules. The particular analyte molecule may include, but is not limited to, biomolecules such as nucleic acids, proteins, hormones, sugars, and metabolites. The ligand may include, but is not limited to, antibodies, receptors, and nucleic acids. Techniques for functionalizing surfaces for attachment of particular analyte molecules thereto have been researched and developed extensively in the art of biosensors and bioassays and can be employed.

SERS system 100 further comprises an actuator 110 that periodically deforms the SERS-active structure 102 at an actuation frequency $f_{ACT}$ under the control of an actuation controller 112 coupled to a constant-frequency source 114. It has been found that, due to the high sensitivity of so-called "hot-spot" formation and extinction to even small variations in local arrangements of SERS-active material nanoconfigurations, a substantial degree of variation in the amount of Raman intensification can be achieved at different points in the periodic actuation cycle. By virtue of the sensitivity of the Raman signal enhancement induced by the SERS-active structure 102 to local nanostructural changes thereon, the periodic deformations of the SERS-active structure 102 cause corresponding periodic variations in the Raman radiation R.

SERS system 100 further comprises a synchronous measuring device 116 receiving the Raman radiation R scattered from the analyte molecules A and generating therefrom at least one Raman signal measurement, which is illustrated by an output block 121 in FIG. 1. The synchronous measuring device 116 operates synchronously with the actuation frequency $f_{ACT}$. The synchronous measuring device 116 comprises a Raman spectrum detector 118 receiving the Raman radiation R and generating therefrom a spectral detection result, which is illustrated by an intermediate block 119 in FIG. 1. The synchronous measuring device 116 further comprises a synchronous detector 120 coupled to receive a reference frequency from the constant-frequency source 114, the reference frequency being equal to the actuation frequency $f_{ACT}$ at which the actuator 110 operates. The synchronous detector 120 receives the spectral detection result 119 and generates therefrom the Raman signal measurement result 121.

Typically, the Raman scattered photons are scattered isotropically from the analyte molecules. Accordingly, the particular angular position of the Raman spectrum detector 118 relative to the radiation source 108 and SERS-active structure 102 often does not substantially affect the intensity of Raman signal received. The Raman spectrum detector 118 optically filters out any Rayleigh component of the scattered radiation and detects an intensity of the Raman scattered radiation R for each wavelength near the incident wavelength. The Raman spectrum detector 118 can be an off-the-shelf unit that spatially separates the Raman radiation according to wavelength (e.g., using one or more prisms and/or gratings) and then detects an intensity at each wavelength using a CCD detector array. However, any of a variety of different Raman detector types can be used without departing from the scope of the present teachings. Preferably, the Raman spectrum detector 118 has a fast time response relative to the actuation period ($1/f_{ACT}$) of the actuator 110, such that an accurate time signal is provided for each measured wavelength (Raman shift, wavenumber, frequency) of the Raman radiation. For one embodiment, the Raman spectrum detector 118 is capable of providing time samples of each measured wavelength of the Raman spectrum at a rate that is at least twice as high as the highest time rate of change for that wavelength, which will usually be some harmonic of the actuation frequency $f_{ACT}$.

Figure 3:
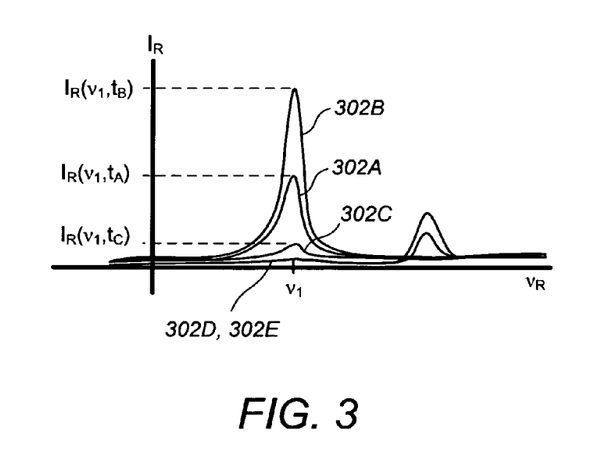
FIG. 3 illustrates conceptual examples of Raman spectra associated with the SERS-active structure of FIGS. 2A-2E.

FIGS. 2A-2E illustrate conceptual side views of the SERS-active structure 102 at points in time $t_A$ through $t_E$, respectively, within a common half-period of the periodic deformations thereof, as well as conceptual symbols of Raman radiation emanating therefrom at those points in time. FIG. 3 illustrates conceptual plots 302A-302E of a time-varying Raman spectrum $I_R(\nu,t)$ at the time points $t_A$ through $t_E$, respectively. Because of the periodicity of the deformations, which repeat every ($1/f_{ACT}$) seconds, the points in time $t_A$ through $t_E$ can be equivalently expressed as the phase angles $\theta_A$ through $\theta_E$ illustrated in FIGS. 2A-2E, respectively.

As used herein, spectral detection result refers to a time signal instantaneously representative of one or more quantitative characteristics of the Raman spectrum $I_R(\nu,t)$. One example of a spectral detection result is a time signal having a value corresponding to a height of the Raman spectrum $I_R(\nu,t)$ at a particular Raman shift $\nu_1$, and is denoted by $I_R(\nu_1, t)$ in FIG. 3 and by the symbol $R_{\nu_1}$ in FIGS. 2A-2E. The spectral detection result $I_R(\nu_1, t)$ is likewise periodic at a frequency of $f_{ACT}$. Other examples of spectral detection results useful in this and other embodiments can include an instantaneous maximum magnitude of the Raman spectrum $I_R(\nu,t)$ (i.e., the maximum value regardless of the wavenumber at which that maximum appears), a combined magnitude of the two highest peaks of the Raman spectrum $I_R(\nu,t)$ at any particular point in time, and a combined spectral energy over the entire Raman spectrum $I_R(\nu,t)$ (e.g., an area underneath the curve $I_R(\nu,t)$) at any particular point in time.

Figure 4:
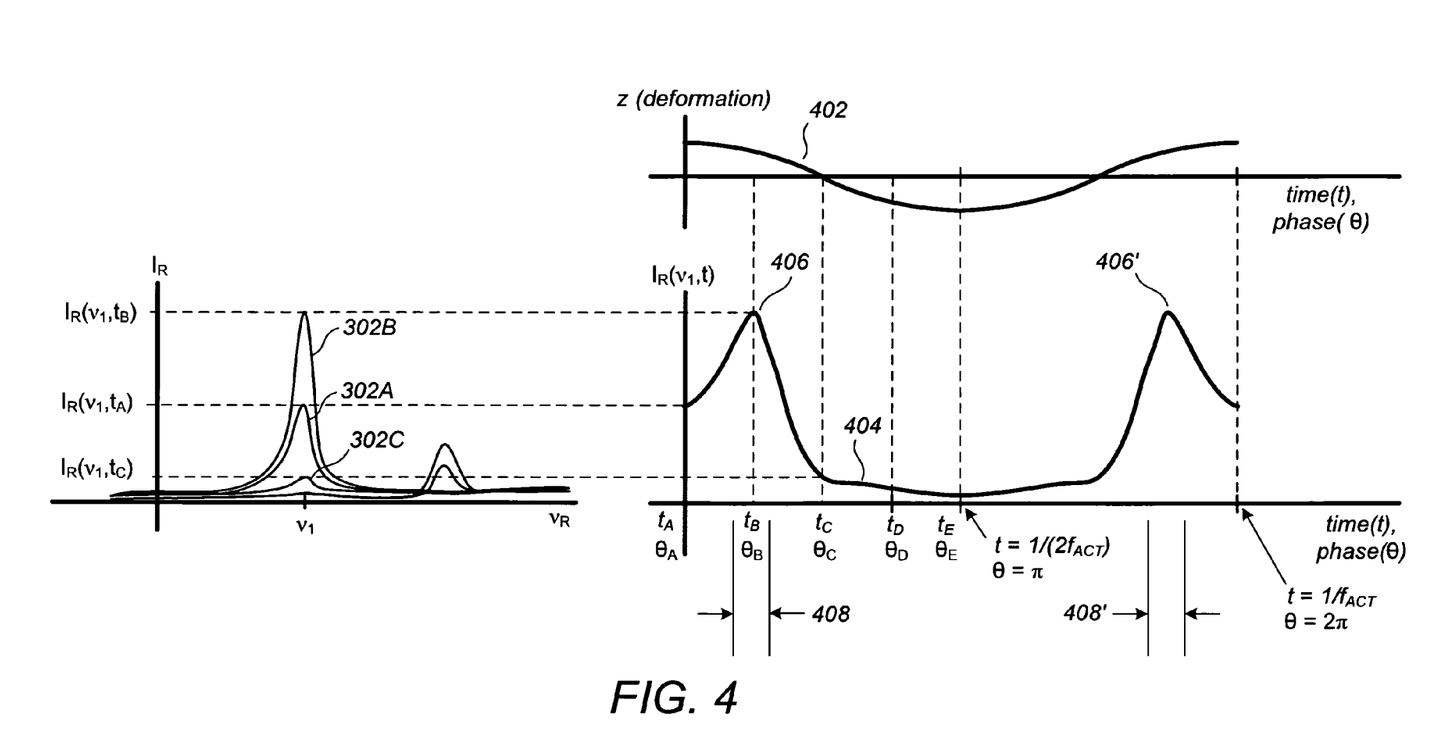
FIG. 4 illustrates a spectral plot and time plots associated with one or more embodiments.

FIG. 4 illustrates a first time plot 402 representing the deformation "z" of the SERS-active substrate 102 over one actuation period, which is of the duration ($1/f_{ACT}$). FIG. 4 also illustrates a second time plot 404 of the spectral detection result $I_R(\nu_1, t)$ over that same time period, as well as a repeated version of the Raman spectra from FIG. 3 drawn on the left side for illustration purposes. As illustrated in FIGS. 2A-2E, FIG. 3, and FIG. 4, the radiation at Raman shift $\nu_1$ passes through a peak value 406 at a phase angle $\theta_B$ within a peak interval 408 during the first half-period ($\frac{1}{2}f_{ACT}$) of the oscillation of the SERS-active substrate 102. The radiation at Raman shift $\nu_1$ further passes through a corresponding peak value 406' at a phase angle ($2\pi-\theta_B$) within a peak interval 408' during the second half-period of the oscillation.

According to one embodiment, the synchronous detector 120 comprises a phase sensitive detection (PSD) device that is phase-matched to detect the spectral detection result $I_R(\nu_1, t)$ (plot 404) during the peak interval 408 of each period thereof. Optionally, the PSD device is also phase-matched to detect the spectral detection result $I_R(\nu_1, t)$ (plot 404) during the corresponding peak interval 408' of each period thereof. For one embodiment, the output of the PSD device, which thus consists of the spectral detection result $I_R(\nu_1, t)$ as measured only during the "best" deformation of the SERS-active structure 102, is then provided as the desired Raman signal measurement at block 121 of FIG. 1. Any of a variety of optional filtering processes, such as a low-pass filter for smoothing out the result, can be applied to the output of the PSD device without departing from the scope of the present teachings.

One particular advantage (among other advantages) of periodically deforming the SERS-active structure and then performing phase-sensitive detection on spectral detection results therefrom relates to noise reduction. For a static SERS-active structure fixed at a single deformation angle, several factors can contribute to noise in the spectral detection results, even where that deformation amount is fixed at an "optimal" or "best" deformation. Examples of such noise sources include perturbations in the excitation radiation frequency, ambient temperature variations, stray environmental mechanical vibrations, stray radiation from visible illumination sources, and induced fluorescence in the analyte and/or contaminant molecules. Periodic deformation of the SERS-active structure and corresponding phase sensitive detection of the spectral detection result bring about noise reduction effects analogous to the way lock-in amplification and phase-sensitive detection alleviate noise effects for periodic signals obscured by noise. Noise alleviation in accordance with the lock-in principle can include 1/f noise, random noise, transient noise, incoherent discrete frequency noise, and noise at harmonics of the measurement frequency.

PSD devices and algorithms, both analog and digital, are known in various different technological contexts and could be implemented in the context of the described embodiments by a person skilled in the art without undue experimentation in view of the present disclosure. It is to be appreciated, however, that the scope of the present teachings is not limited to the use of PSD detection. In other embodiments, similar functionalities and noise reduction effects are achieved using a synchronous detector 120 that comprises a homodyne detector having a reference frequency equal to the actuation frequency $f_{ACT}$. In one example of a homodyne detection embodiment, the spectral detection result is mixed with a periodic reference signal at the reference frequency, and the result is low-pass filtered. In other embodiments, analogous functionalities and noise reduction effects are achieved using a synchronous detector 120 that comprises a heterodyne detector having first and second reference frequencies that sum to the actuation frequency $f_{ACT}$. In one example of a heterodyne detection embodiment, the spectral detection result is mixed with a first periodic reference signal at the first reference frequency to produce a first signal, the first signal is bandpass filtered and mixed with a second periodic reference signal at the second reference frequency to produce a second signal, and then the second signal is low-pass filtered.

The synchronous detector 120, actuation controller 112, and constant frequency source 114 can be implemented as discrete hardware components or, alternatively, can be collectively embodied in a computer program product stored on a digital computing device that receives the spectral detection result 119 in digital format and provides the Raman signal measurement 121 in digital format. Components of the Raman spectrum detector 118 that process CCD detection outputs (or other physical detector outputs) into numerical expressions for the spectral detection result 119 can also be integrated into the computer program product.

Figure 5:
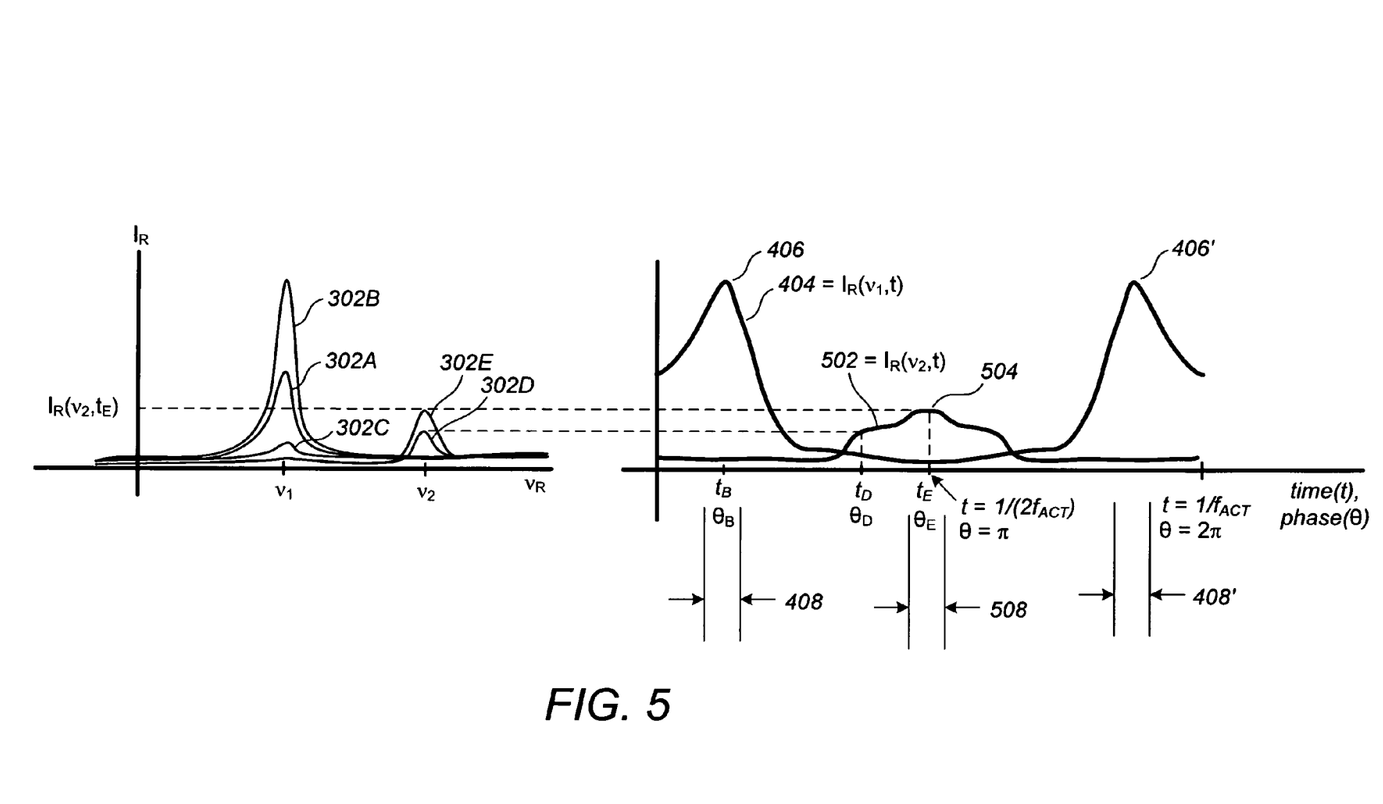
FIG. 5 illustrates a spectral plot and time plots associated with one or more embodiments.

FIG. 5 illustrates another repeated version of the Raman spectra from FIG. 3, a repeated version of the plot 404 of the spectral magnitude $I_R(\nu_1, t)$ over one periodic interval ($1/f_{ACT}$), and a time plot 504 of a second spectral magnitude $I_R(\nu_2, t)$ representative of the magnitude of the Raman spectrum $I_R(\nu,t)$ at a second Raman shift $\nu_2$. Depending on the particular nature of the SERS-active structures and the analyte in question, it may be the case that a first deformation amount that causes a temporal peak for a first Raman shift could be different than a second deformation amount that causes a temporal peak for a second Raman shift. Thus, for example, illustrated in FIG. 5 is an example for which the second spectral magnitude $I_R(\nu_2, t)$ experiences a temporal peak 504 at a different time $t_E$ (and different phase angle $\theta_E$) within a different time interval 508 than for the peak of the first spectral magnitude $I_R(\nu_1, t)$.

According to one embodiment, the synchronous detector 120 is further configured to detect the second spectral magnitude $I_R(\nu_2, t)$ within the time interval 508 along with the first spectral magnitude $I_R(\nu_1, t)$ within the time interval(s) 408 (408'). Thus, for example, in the particular context of PSD detection, where there is a spectral detection result comprising both a first spectral magnitude $I_R(\nu_1, t)$ at a first Raman scattering frequency (Raman shift $\nu_1$) and a second spectral magnitude $I_R(\nu_2, t)$ at a second Raman scattering frequency (Raman shift $\nu_2$), each of the first and second spectral magnitudes varying periodically at the actuation frequency according to the periodic deformations of the SERS-active structure and respectively exhibiting at least one peak value (406, 504) within at least one peak interval (408, 508) of each period thereof, provided is a synchronous detector that comprises a first PSD device phase matched to detect the first spectral magnitude $I_R(\nu_1, t)$ during the peak interval 408 of each period thereof; and that further comprises a second PSD device phase matched to detect the second spectral magnitude $I_R(\nu_2, t)$ during the peak interval 508 of each period thereof. Extensions to spectral detection results comprising three or more different spectral magnitudes (or other quantitative aspects of the Raman spectra $I_R(\nu, t)$ captured by the Raman spectrum detector 118) are also within the scope of the present teachings.

Figure 6:
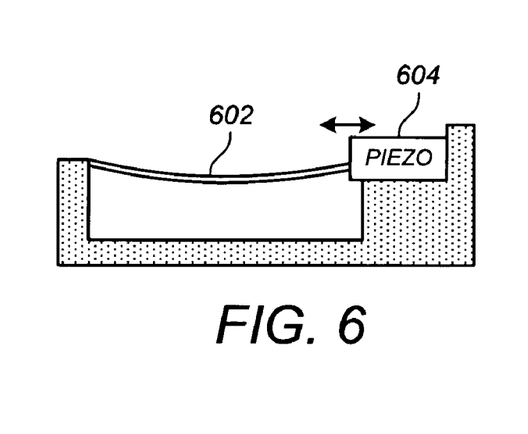
FIG. 6 illustrates an apparatus for facilitating SERS according to an embodiment having piezoelectrically actuated deformation of a SERS-active structure.

FIGS. 6-9 illustrate some examples of different actuation configurations that can be used in accordance with one or more of the embodiments, although it is to be appreciated that many other configurations based on a variety of different actuation methodologies may be used without departing from the scope of the present teachings. The actuation configurations of FIGS. 6-9 can be used as alternatives to, or in conjunction with, the actuation configuration shown in FIG. 1, supra, with different ones accommodating different actuation frequencies including, but not limited to, a range of 1 Hz-100 MHz. FIG. 6 illustrates one such exemplary actuation scheme in which a concavity (or a convexity) of a SERS-active structure 602 having a generally rigid substrate is controlled by a piezoelectric actuator 604 that moves in an in-plane direction. Advantageously, because only a modest amount of deformation is usually required (e.g., on the order of 1 percent or less), the substrate can comprise any of a variety of different solid materials, even many crystalline materials, without incurring breakage in the deformation process.

Figure 7:
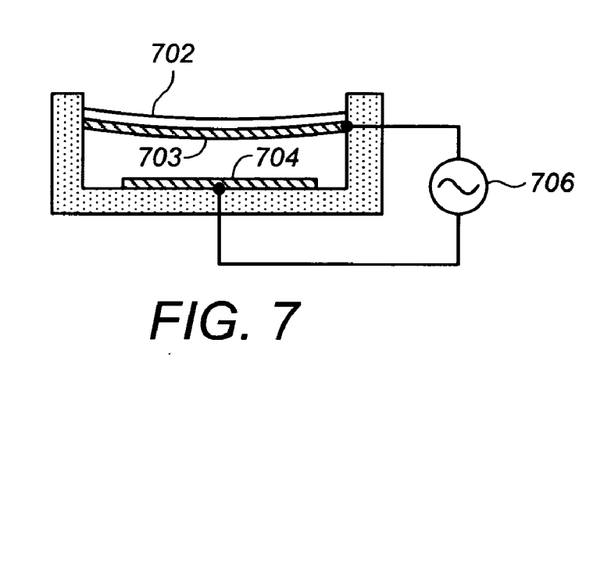
FIG. 7 illustrates an apparatus for facilitating SERS according to an embodiment having electrostatically actuated deformation of a SERS-active structure.

FIG. 7 illustrates another exemplary actuation scheme in which a concavity (or a convexity) of a SERS-active structure 702 is electrostatically actuated. A metal layer 703 is attached to a substrate of the SERS-active structure 702, a metal plate 704 is attached to a nearby fixed surface, and a voltage is applied between the metal layer 703 and the metal plate 704, the SERS-active structure 702 deforming by electrostatic force between the metal layer 703 and metal plate 704. Any of a variety of other types of microelectromechanical (MEMS) actuation schemes are also within the scope of the present teachings.

Figure 8:
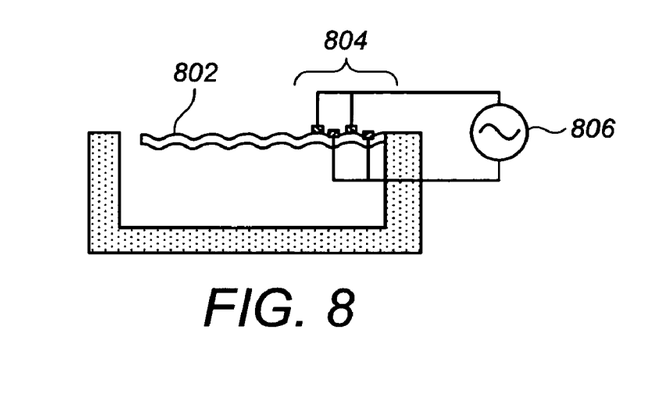
FIG. 8 illustrates an apparatus for facilitating SERS according to an embodiment in which deformation of a SERS-active structure is induced by a surface acoustic wave (SAW) actuator.

FIG. 8 illustrates another exemplary actuation scheme in which periodic local deformations in a SERS-active structure 802 are induced by a surface acoustic wave (SAW) generator 804 coupled to an actuation voltage source 806. Actuation by surface acoustic waves can be particularly desirable where very high actuation frequencies are desired. Any of a variety of SAW actuation schemes can be used, even those having actuation frequencies up to 100 MHz and beyond. Because of the high sensitivity of many SERS-active materials to local changes in microstructural/nanostructural configurations, even very small amplitude deformations as would be associated with very high actuation frequencies can induce enough local deformation to cause appreciable modulation of the Raman spectra sufficient for bringing about lock-in noise reduction effects and/or other benefits of periodic actuation and synchronous measurement.

Figure 9:
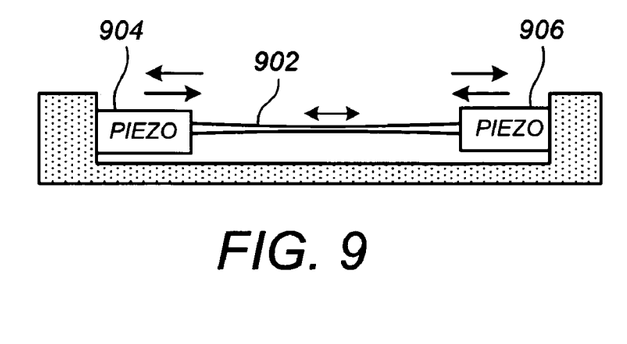
FIG. 9 illustrates an apparatus for facilitating SERS according to an embodiment having piezoelectrically actuated in-plane expansion and/or contraction of a SERS-active structure.

FIG. 9 illustrates a SERS facilitation apparatus according to an embodiment in which a SERS-active structure 902 comprises a stretchable polymeric membrane upon which is disposed spatial arrangements of SERS-active material. The spatial arrangement of the SERS-active material is varied in accordance with a stretching and/or relaxation of the polymeric membrane by piezoelectric actuators 904 and 906, thereby providing variation in the amount of Raman intensification provided by the SERS-active structure 902. In another embodiment (not shown) a concavity (or a convexity) of a SERS-active structure is microfluidically actuated, e.g., by a fluid pump coupled to an expandable reservoir device against which the SERS-active structure is mounted. The use of microfluidic actuation can be less advantageous than mechanical or electromagnetic actuation in circumstances where high actuation frequencies are desired.

Figure 10:
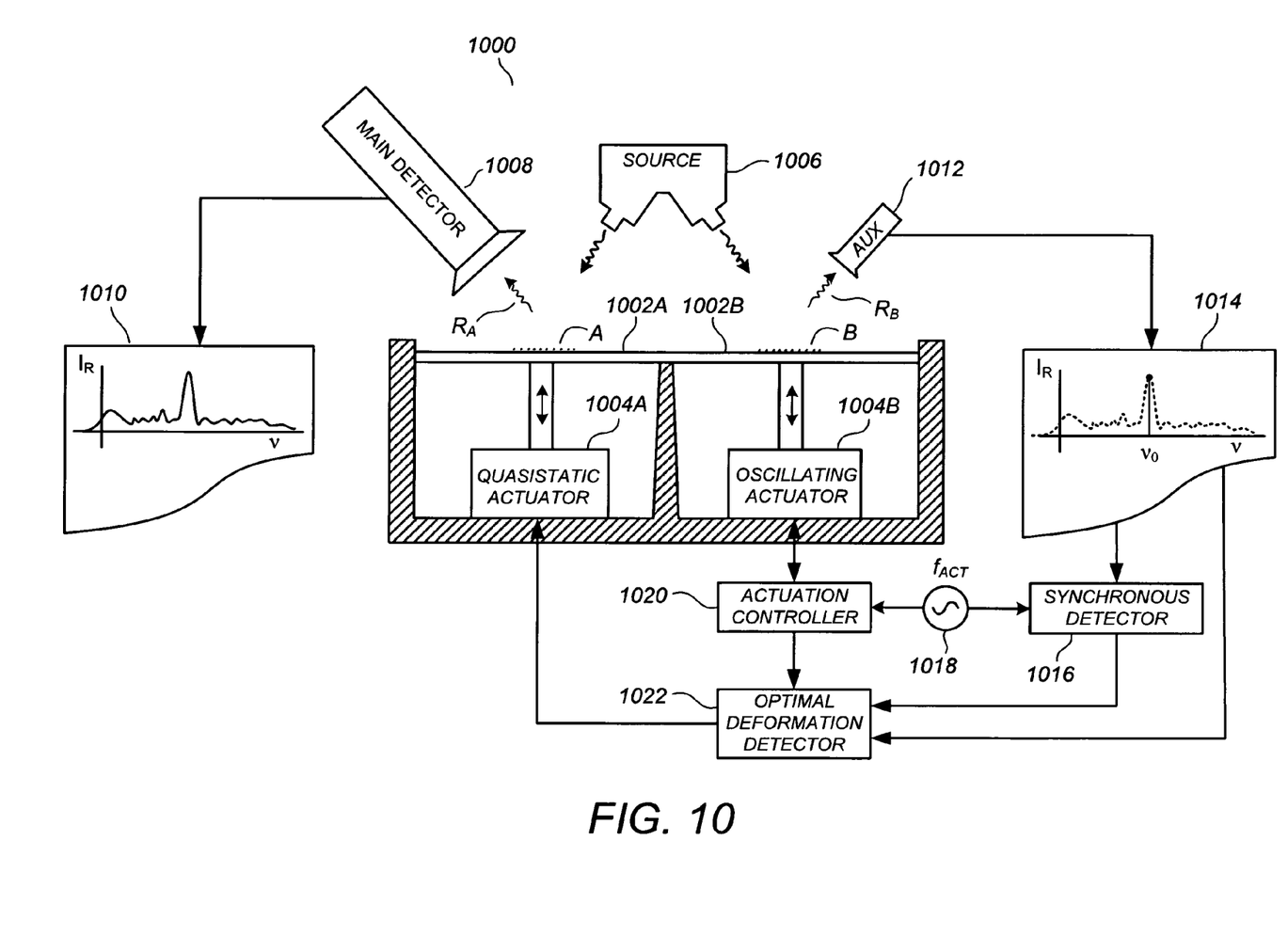
FIG. 10 illustrates a SERS system including an apparatus for facilitating SERS according to an embodiment.

FIG. 10 illustrates a SERS system 1000 including an apparatus for facilitating SERS according to an embodiment in which two (2) actuators are provided that deform different parts of a single SERS-active structure or, alternatively, that deform two different SERS-active structures that are similar in structure and performance. One of the actuators is associated with a "DC" or quasistatic actuation of a "main" or "primary" SERS-active structure and sample, while the other actuator is an "AC" or oscillatory actuator associated with a "secondary" or "pilot" SERS-active structure and sample. According to an embodiment, information that is continuously "learned" from the oscillating pilot SERS-active structure and sample, which operates in a lock-in fashion similar to that of the embodiment of FIG. 1, supra, is then provided to the primary actuator, which can continually adjust, in a "DC" or quasistatic manner, the position of the primary SERS-active structure to the best position for the strongest Raman spectrum readings.

More particularly, provided is a first SERS-active structure 1002B (or portion of a larger such structure) containing a reference analyte "B", a first actuation device 1004B, an actuation controller 1020, a first Raman detector 1012, a constant-frequency source 1018, and a synchronous detector 1016 that collectively operate in a manner similar to the device of FIG. 1, supra, with an intermediate, oscillatory spectral detection 1014 result being shown at block 1014 and with the synchronously-processed Raman measurement result being an output of the synchronous detector 1016. A radiation source 1006 irradiates the analyte "B" to generate Raman radiation $R_B$. Also provided is a second SERS-active structure 1002A (or portion of a larger such structure) similar to the first SERS-active structure 1002B near which a second plurality "A" of analyte molecules is disposed. The radiation source 1006 also irradiates the analyte "A" to generate Raman radiation $R_A$.

Also provided is a second actuation device 1004A in actuable communication with the second SERS-active structure 1002A, the second actuation device 1004A deforming the second SERS-active structure 1002A quasistatically relative to the actuation frequency $f_{ACT}$ of the first actuation device 1004B. Also provided is a second Raman signal detector 1008 receiving second Raman radiation $R_A$ scattered from the second plurality of analyte molecules "A" and generating therefrom a quasistatic spectral detection result 1010, which represents the "main" or "primary" output of the SERS system 1000. Also provided is an optimal deformation detector 1022 for providing an optimal deformation level for the second actuation device 1004A based at least in part on the spectral detection result 1014 from the first Raman signal detector 1012 and the synchronously-processed Raman measurement result from the synchronous detection device 1016. For one preferred embodiment, the first plurality of analyte molecules "B" includes molecules of a target substance to be detected in the second plurality of molecules "A." For one embodiment, because the first Raman detector 1012 is only being used for "pilot" purposes, it is configured for detecting a relatively sparse subset of Raman scattering radiation frequencies in comparison to the second Raman signal detector 1008, and therefore can be much less expensive than the second Raman signal detector 1008.

Whereas many alterations and modifications of the embodiments will no doubt become apparent to a person of ordinary skill in the art after having read the foregoing description, it is to be understood that the particular embodiments shown and described by way of illustration are in no way intended to be considered limiting. By way of example, multiple similar or different deformable SERS-active substrates can be arrayed together and jointly or separately actuated for use in conjunction with a single laser source or multiple laser sources to achieve any of a variety of goals including, but not limited to, portability, dependability, reusability, cost efficiency, calibration reliability, and/or adaptability for differing analyte molecule types, without departing from the scope of the present teachings.

By way of further example, while one or more spectral detection results supra are described as comprising various quantitative features, or combinations of features, of the time-oscillatory Raman spectrum $I_R(v,t)$, it is to be appreciated that the spectral detection result that is synchronously processed can actually include the entire Raman spectrum $I_R(v,t)$ itself, wherein each time signal for each different Raman shift v is processed and output as a Raman measurement result. By way of still further example, as the terms synchronized and synchronicity are used herein, it is to be appreciated that a synchronous detector is not required to function exclusively at the baseband actuation frequency to be considered as being in synchronicity or synchronized therewith, but can be operative at a harmonic of the actuation frequency, for example. Likewise, it is to be appreciated that no preordained phase relationship between the reference oscillator and the actuation oscillations are implicated by virtue of the terms in synchronicity or synchronized with. By way of even further example, the present teachings can be used with hyper Raman spectroscopy in which higher order harmonics of the source radiation are considered. Thus, reference to the details of the described embodiments are not intended to limit their scope.

What is claimed is:

1. An apparatus for facilitating surface-enhanced Raman spectroscopy (SERS), comprising:
    a SERS-active structure near which a plurality of analyte molecules is disposed;
    an actuation device in actuable communication with the SERS-active structure, the actuation device periodically deforming the SERS-active structure at an actuation frequency; and
    a synchronous measuring device receiving Raman radiation scattered from the analyte molecules and generating therefrom at least one Raman signal measurement, wherein said synchronous measuring device is synchronized with said actuation frequency.

2. The apparatus of claim 1, wherein said synchronous measuring device comprises:
    a Raman signal detector receiving said Raman radiation and generating therefrom at least one spectral detection result; and
    a synchronous detector operating at said actuation frequency, said synchronous detector receiving said at least one spectral detection result and generating therefrom said at least one Raman signal measurement.

3. The apparatus of claim 2, said at least one spectral detection result varying periodically at the actuation frequency according to said periodic deformations of the SERS-active structure and exhibiting at least one peak value within at least one peak interval of each period thereof, wherein said synchronous detector comprises a phase sensitive detection device that is phase matched to detect said at least one spectral detection result during said at least one peak interval of each period thereof.

4. The apparatus of claim 2, said at least one spectral detection result comprising a first spectral magnitude at a first Raman scattering frequency and a second spectral magnitude at a second Raman scattering frequency, each of said first and second spectral magnitudes varying periodically at the actuation frequency according to said periodic deformations of the SERS-active structure and respectively exhibiting at least one peak value within at least one peak interval of each period thereof, wherein said synchronous detector comprises:
    a first phase sensitive detection device phase matched to detect said first spectral magnitude during said at least one peak interval of each period thereof; and
    a second phase sensitive detection device phase matched to detect said second spectral magnitude during said at least one peak interval of each period thereof.

5. The apparatus of claim 3, wherein said synchronous detector is embodied in a computer program product stored on a digital computing device that receives said at least one spectral detection result in digital format and provides said at least one Raman signal measurement in digital format.

6. The apparatus of claim 2, wherein said at least one spectral detection result is representative of one or more of an energy of said Raman radiation at a single predetermined scattering frequency, an energy of said Raman radiation at a peak scattering frequency, and a combined spectral energy of said Raman radiation across a predetermined range of Raman scattering frequencies.

7. The apparatus of claim 2, said Raman signal detector, said Raman radiation, said actuation device, said SERS-active structure, and said plurality of analyte molecules being a first Raman signal detector, first Raman radiation, a first actuation device, a first SERS-active structure, and a first plurality of analyte molecules, respectively, the apparatus further comprising:
    a second SERS-active structure similar to said first SERS-active structure near which a second plurality of analyte molecules is disposed;
    a second actuation device in actuable communication with the second SERS-active structure, the second actuation device deforming the second SERS-active structure quasistatically relative to said actuation frequency of said first actuation device;
a second Raman signal detector receiving second Raman radiation scattered from said second plurality of analyte molecules and generating therefrom a quasistatic spectral detection result; and
an optimal deformation detector for providing an optimal deformation level for said second actuation device based at least in part on said spectral detection result from said first Raman signal detector and said at least one Raman signal measurement from said synchronous detection device.

8. The apparatus of claim 7, wherein said first plurality of analyte molecules includes molecules of a target substance to be detected in said second plurality of molecules by said quasistatic spectral detection result, and wherein said first Raman signal detector is configured for detecting a relatively sparse subset of Raman scattering radiation frequencies in comparison to said second Raman signal detector.

9. The apparatus of claim 2, wherein said synchronous detector comprises one of a homodyne detector having a first reference frequency equal to said actuation frequency and a heterodyne detector having second and third reference frequencies that sum to said actuation frequency.

10. The apparatus of claim 1, wherein said actuation frequency is in a range of 1 Hz-100 MHz, and wherein said actuation device is selected from the group consisting of: surface acoustic wave actuators, piezoelectric actuators, microelectromechanical actuators, and microfluidic actuators.

11. A method for facilitating surface-enhanced Raman spectroscopy (SERS), comprising:
receiving a plurality of analyte molecules for attachment near a SERS-active structure;
periodically deforming the SERS-active structure at an actuation frequency in a vicinity of the analyte molecules; and
receiving Raman radiation scattered from the analyte molecules at a synchronous measuring device that generates at least one Raman signal measurement therefrom, the synchronous measuring device being synchronized with said actuation frequency.

12. The method of claim 11, said synchronous measuring device comprising a Raman signal detector that generates at least one spectral detection result from said received Raman radiation, said synchronous measuring device further comprising a synchronous detector receiving said at least one spectral detection result and generating therefrom said at least one Raman signal measurement, said synchronous detector operating at said actuation frequency.

13. The method of claim 12, wherein said synchronous detector comprises one of a homodyne detector having a first reference frequency equal to said actuation frequency and a heterodyne detector having second and third reference frequencies that sum to said actuation frequency.

14. The method of claim 12, said at least one spectral detection result varying periodically at the actuation frequency according to said periodic deformations of the SERS-active structure and exhibiting at least one peak value within at least one peak interval of each period thereof, wherein said synchronous detector uses phase sensitive detection to detect said at least one spectral detection result during said at least one peak interval of each period thereof.

15. The method of claim 12, said at least one spectral detection result comprising a first spectral magnitude at a first Raman scattering frequency and a second spectral magnitude at a second Raman scattering frequency, each of said first and second spectral magnitudes varying periodically at the actuation frequency according to said periodic deformations of the SERS-active structure and respectively exhibiting at least one peak value within at least one peak interval of each period thereof, wherein said synchronous detector uses phase sensitive detection to detect said first and second spectral magnitudes during said respective peak intervals of each period thereof.

16. The method of claim 12, said Raman radiation, said SERS-active structure, and said plurality of analyte molecules being first Raman radiation, a first SERS-active structure, and a first plurality of analyte molecules, respectively, the method further comprising:
detecting an optimal deformation amount for said first SERS-active structure based at least in part on said spectral detection result from said first Raman signal detector and said at least one Raman signal measurement from said synchronous detection device;
quasistatically deforming by said optimal deformation amount a second SERS-active structure similar to said first SERS-active structure near which a second plurality of analyte molecules is disposed; and
receiving second Raman radiation scattered from said second plurality of analyte molecules and generating therefrom a quasistatic spectral detection result;
wherein said first plurality of analyte molecules includes molecules of a target substance to be detected in said second plurality of molecules by said quasistatic spectral detection result.

17. The method of claim 11, wherein said actuation frequency is in a range of 1 Hz-100 MHz, and wherein said actuation device is selected from the group consisting of: surface acoustic wave actuators, piezoelectric actuators, microelectromechanical actuators, and microfluidic actuators.

18. An apparatus, comprising:
a SERS-active structure near which a plurality of analyte molecules is disposed;
means for detecting Raman radiation scattered from said analyte molecules;
means for periodically deforming the SERS-active structure at an actuation frequency to cause an output of said means for detecting to be periodic at said actuation frequency; and
means for synchronous processing of said output of said means for detecting to generate therefrom a Raman signal measurement, said means for synchronous processing using a reference frequency equal to said actuation frequency.

19. The apparatus of claim 18, wherein said means for synchronous processing comprises one of a phase sensitive detection device, a homodyne detection device, and a heterodyne detection device.

20. The apparatus of claim 18, wherein said output of said means for detecting is selected from the group consisting of an energy of said Raman radiation at a single predetermined scattering frequency, an energy of said Raman radiation at a peak scattering frequency, and a combined spectral energy of said Raman radiation across a predetermined range of Raman scattering frequencies, wherein said wherein said actuation frequency is in a range of 1 Hz-100 MHz, and wherein said means for periodically deforming includes one or more of a piezoelectric actuator, a surface acoustic wave actuator, a microelectromechanical actuator, and a microfluidic actuator.

* * * * *

UNITED STATES PATENT AND TRADEMARK OFFICE
CERTIFICATE OF CORRECTION

PATENT NO. : 7,609,377 B2
APPLICATION NO. : 11/796455
DATED : October 27, 2009
INVENTOR(S) : Wei Wu et al.

Page 1 of 1

It is certified that error appears in the above-identified patent and that said Letters Patent is hereby corrected as shown below:

In column 12, line 61, in Claim 20, after "wherein said" delete "wherein said".

Signed and Sealed this

Twentieth Day of April, 2010

David J. Kappos
*Director of the United States Patent and Trademark Office*